United States Patent [19]

Kamienski et al.

[11] 4,069,267

[45] Jan. 17, 1978

[54] STABLE DIORGANOMAGNESIUM COMPOSITIONS

[75] Inventors: Conrad W. Kamienski, Gastonia, N.C.; Bobby Joe McElroy, York, S.C.; Ricardo O. Bach, Gastonia, N.C.

[73] Assignee: Lithium Corporation of America, Gastonia, N.C.

[21] Appl. No.: 736,262

[22] Filed: Oct. 27, 1976

[51] Int. Cl.$^2$ ............................................... C07F 3/02
[52] U.S. Cl. ........................... 260/665 R; 252/431 R
[58] Field of Search ................. 260/665 R; 252/431 R

[56] References Cited

U.S. PATENT DOCUMENTS

| | | | |
|---|---|---|---|
| 3,646,231 | 2/1972 | Kamienski et al. | 260/665 R |
| 3,737,393 | 6/1973 | de Vries | 252/431 R |
| 3,742,077 | 6/1973 | Kamienski et al. | 260/668 B |
| 3,755,478 | 8/1973 | Kamienski et al. | 260/665 R |
| 3,766,280 | 10/1973 | Kamienski et al. | 260/665 R |

OTHER PUBLICATIONS

Malpass, et al., J. Orgonometallic Chem. 93, pp. 1–8, (1975).
Glaze, et al., J. Organometal Chem. 5, pp. 477–480, (1966).

*Primary Examiner*—Helen M. S. Sneed
*Attorney, Agent, or Firm*—Wallenstein, Spangenberg, Hattis & Strampel

[57] ABSTRACT

Stable diorganomagnesiums are prepared which are soluble in acyclic liquid hydrocarbons and represent novel and highly useful compositions. They are prepared, for instance, by forming a mixture of magnesium metal powder in an acyclic liquid hydrocarbon to which are added a $C_1$–$C_4$ n-alkyl halide, such as n-butyl chloride, and a n-alkyl halide containing at least 6 carbon atoms, such as n-octyl chloride, and effecting reaction to convert them to their corresponding dialkylmagnesiums. Then, a secondary or tertiary organolithium compound, such as sec- or tert-butyllithium, is added, in the form of a solution in an acyclic liquid hydrocarbon, and the byproduct halide salts which were formed and are present in the reaction mixture are separated from the resulting stable solution of the diorganomagnesium complex by filtration or by equivalent separation procedures. The resulting stable solutions of the said complex of diorganomagnesiums can be produced in a variety of acyclic liquid hydrocarbons, or mixtures of said acyclic liquid hydrocarbons, including those which are of linear or branched character.

13 Claims, No Drawings

STABLE DIORGANOMAGNESIUM COMPOSITIONS

BACKGROUND OF THE INVENTION

1. Field of the Invention

The present invention deals with the preparation of certain novel dialkylmagnesiums, commonly designated as magnesium alkyls, and methods for making such reagents and compositions containing said reagents.

Organomagnesium halides, which can be represented by the formula RMgX, where X is halogen, commonly known as Grignard reagents, have wide utility in chemical reactions. By comparison with Grignard reagents, dialkylmagnesium reagents have found less widespread use although such latter compounds commonly undergo reactions analogous or similar to those of Grignard reagents. Primary reasons for the use heretofore of the Grignard reagents over dialkylmagnesiums lies in the fact that, previously, there has been no easy or satisfactory method by which large amounts of dialkylmagnesiums could be prepared, and in certain deficiencies of the dialkylmagnesiums. The present invention involves new techniques for the preparation of novel dialkylmagnesiums relatively simply, in large quantities and free from instability disadvantages characterizing prior dialkylmagnesiums, and makes feasible their effective and economical use for purposes now served by Grignard reagents and by other organometallic compounds, particularly alkyllithiums. While both Grignard reagents and alkyllithiums are presently commercially available, our invention makes possible the production of dialkylmagnesiums at a cost comparable to or less, commercially, than either the Grignard reagents or alkyllithiums if the cost is calculated per organic group (R) and includes both ingredient costs and shipping costs. Furthermore, in certain instances, the dialkylmagnesiums are superior for chemical reasons. Relative to alkyllithiums, a particularly important advantage of the dialkylmagnesiums of the present invention is their greater thermal stability and the lesser pyrophoric character of their solutions and, in this connection, it may be pointed out that stable concentrated solutions of dialkylmagnesiums in saturated acyclic liquid hydrocarbons are not known actually to have been previously prepared. In addition to the values of such latter solutions based on their convenience as easily handled sources of dialkylmagnesiums for use in carrying out known types of reactions, said acyclic liquid hydrocarbon solutions are particularly valuable insofar as they afford dialkylmagnesiums for one-step chemical reactions not attainable with dialkylmagnesiums in othe solvents. The novel dialkylmagnesiums of the present invention constitute a new catalyst system for multi-step reactions such as oligomerizations and polymerizations; and, also, they may be used as basic materials from which other catalyst systems may conveniently be prepared. Typical polymerization processes for which these novel dialkylmagnesiums are very useful are stereo-specific polymerizations of α-olefins as, for example, ethylene and propylene, and conjugated dienes as, for example, 1,3-butadiene and isoprene. No Lewis base is employed in such processes, the polymerization being run in a liquid acyclic hydrocarbon solvent. such stereo-specific polymerizations of isoprene, for example, yield synthetic rubbers very much like natural Hevea rubber, these rubbers having almost exclusively a cis-1,4- mode of enchainment.

2. Description of Prior Art

U.S. Pat. Nos. 3,646,231; 3,742,077; 3,755,478 and 3,766,280 are illustrative of disclosures of heretofore known procedures for the preparation of liquid hydrocarbon-soluble diorganomagnesiums.

Thus, for instance, as shown, in U.S. Pat. No. 3,742,077, it is already known, among other things, to prepare hydrocarbon-soluble complexes of hydrocarbon-insoluble primary, linear dialkylmagnesiums, as as di-n-butylmagnesium, with hydrocarbon-soluble secondary branched dialkylmagnesiums, the initial linear dialkylmagnesium compound being prepared directly in a liquid hydrocarbon-solvent such as methylcyclohexane, hexane, benzene or toluene by reacting magnesium metal in said solvent with n-butyl chloride, followed by reaction with a secondary or tertiary alkyllithium to react with byproduct $MgCl_2$ formed in the first step. The resulting solution, after separation of solids, contains a complex of (a) a primary dialkylmagnesium with (b) a secondary or tertiary dialkylmagnesium. Illustrative complexes disclosed in said patent are those of di-n-amylmagnesium with di-sec-butylmagnesium; di-n-butylmagnesium with di-tert-butylmagnesium; and di-n-butylmagnesium with di-sec-butylmagnesium. These complexes of said patent are also disclosed to be produced by reacting an alkyllithium in sufficient quantity to both react with all of the byproduct $MgCl_2$ and also to form a complex with the so-prepared dialkylmagnesium compounds or, alternatively, to form complexes of the dialkylmagnesium compounds with alkylsodium or alkylpotassium compounds. The complexes are disclosed to be formed and to be soluble in aliphatic and cycloaliphatic solvents such as heptane, hexane, octane, cyclohexane and methylcyclohexane, but particularly desirably in aromatic hydrocarbons such as benzene, toluene, and xylenes, and compatible mixtures of two or more of the aforesaid solvents. The complex compositions of said patent, in the form of their hydrocarbon solutions, are stated to possess a high degree of stability in comparison with the stability of the uncomplexed solid reagents, such as alkylsodiums and alkylpotassiums.

When pure, dry metallic magnesium is treated with an alkyl halide, in a liquid purely hydrocarbon solvent such as heptane, cyclohexane, or toluene, it is found that only certain alkyl halides, for example, those of the normal or unbranched variety, illustrative of which is n-butyl chloride, react to produce the desired dialkylmagnesiums. The resulting products are, generally, viscous mixtures of partially solubilized dialkylmagnesiums accompanied by a precipitate of byproduct magnesium halide. This mixture of products can be converted into a fluid, halide-free solution of dialkylmagnesiums by interaction with an alkyllithium compound with branching at $C_1$ in like hydrocarbon solvents.

The set of reactions describing this heretofore known process is as follows:

(where R and R' are alkyl, X is halogen such as chlorine or bromine, and H.C. is a liquid hydrocarbon solvent).

The resulting hydrocarbon solutions of $R_2Mg \cdot R_2'Mg$, where R' may be n-butyl- or n-amyl, and R is a sec-butyl- or tert-butyl group, possess only a limited solubility in liquid acyclic hydrocarbon solvents, such as n-hexane, n-heptane, or isooctane, generally of the order of 0.5 equivalents (0.25M) per liter of solution, or less, in sharp contradistinction to those dialkylmagnesiums containing both R and R' groups of a branched (at the alphacarbon atom) nature, exemplified, for example, by di-sec-butyl-magnesium or di-tert-butylmagnesium, which are highly soluble, of the order of 2 or 3 moles per liter of solution. However, since such symmetrical, branched dialkylmagnesiums cannot satisfactorily be produced directly from magnesium metal, but, generally speaking, must be less economically produced from activated magnesium halides and more expensive alkyllithiums, an improvement in the solubility in liquid acyclic hydrocarbon solvents of mixed unbranched and branched dialkylmagnesium complexes represents a much desired goal.

Employing the heretofore known techniques described above for their preparation, some dialkylmagnesiums have been found to be insoluble in liquid hydrocarbons, particularly those dialkylmagnesiums with alkyl groups having no branching at the alpha carbon atoms. These insoluble dialkylmagnesiums are represented hereafter as $R_2'Mg$ or $R_2''Mg$ (where R' and R" = methyl, n-butyl and isobutyl, for example). Hydrocarbon solutions of these unsolvated dialkylmagnesiums can be produced by complexation with each other.

Based upon our discoveries, several variant procedures for the preparation of acyclic liquid hydrocarbon solutions of complex dialkylmagnesiums have been evolved.

DESCRIPTION OF OUR INVENTION AND PREFERRED EMBODIMENTS THEREOF

In the practice of our invention, an admixture of linear or n-alkyl halides, possessing carbon number values of at least $C_6$, and generally up to about $C_{18}$, but especially $C_8$ to $C_{10}$, in varying amounts from about 5–50 mol %, with lower linear or n-alkyl ($C_1$–$C_4$) halides, are initially reacted with magnesium metal. Thus, for example, 10 mole % of n-octyl chloride (based on total chloride) with 90 mole % of n-butyl chloride are charged for reaction with magnesium metal in acyclic liquid hydrocarbon solvent media in step 1 (below). After the reaction in step 1 is complete, sec-butyllithium equivalent to 80 to 95 mole % of the total n-alkyl chloride charge is added to the viscous reaction mixture, after which filtration to remove byproduct chloride salts results in the isolation of a clear fluid 1-Normal solution of dibutylmagnesium. The reactions involved in regard to this illustrative composition are shown in the following steps.

Step 1:

Direct Preparation of complex of Di-n-butylmagnesium and Di-n-octylmagnesium $2 CH_3(CH_2)_3Cl + 2 CH_3(CH_2)_7Cl + 4 Mg \rightarrow$
$[CH_3(CH_2)_3]_2Mg \cdot [CH_3(CH_2)_7]_2Mg + 2 MgCl_2$ Step 2:

Reaction of Step 1 Product with Sec-butyllithium $[CH_3(CH_2)_3]_2Mg \cdot [CH_3(CH_2)_7]_2Mg + 2 MgCl_2$

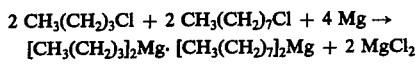

-continued

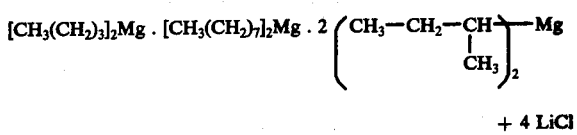

Lower alkyl normal halides ($C_1$–$C_4$), constituting the major portion (50–95 mole %) of the halide charge to be reacted with magnesium metal in an acyclic liquid hydrocarbon solvent medium, may be alkyl chlorides, such as methyl, ethyl, n-propyl, and n-butyl chloride, and the corresponding lower alkyl bromides, or, less desirably, the corresponding lower alkyl iodides.

Normal higher alkyl halides ($C_6$ and above), constituting the minor portion of the halide charge to be reacted with magnesium metal in an acyclic liquid hydrocarbon medium, are exemplified by n-hexyl chloride, n-heptyl chloride, n-octyl chloride, n-nonyl chloride, n-decyl chloride, n-dodecyl chloride and n-tetradecyl chloride, and their corresponding bromides and iodides. Higher carbon number analogues can also be used, such as those of $C_{18}$, but are less desirable due to their lower reactivity and higher cost. Most advantageous are n-octyl and n-decyl halides, (particularly the chlorides and bromides).

Although as much as 50 mole % of these higher n-alkyl halides can be added to the desired lower n-alkyl halide charge to be reacted with magnesium metal, a preferred range is 5–25 mole %, and especially 10–20 mole %, based on the total halide charge.

Although lower carbon number linear dialkylmagnesium compounds, such as di-n-butylmagnesium, when complexed with varying amounts of highly branched (branching at the alpha carbon atoms) dialkylmagnesium compounds, such as di-sec-butylmagnesium, are quite soluble in cyclic solvents such as cyclohexane and benzene (greater than 1-Normal concentrations) these mixed complexes of dialkylmagnesium compounds show only a limited solubility in acyclic liquid hydrocarbons, such as n-pentane, n-hexane, n-heptane, n-octane and their isomeric branched analogues, generally in the order of only about 0.7 normal concentrations or less as indicated by precipitate formation during storage at room temperature.

Moreover, cold storage at 5° C normally employed to prolong the stability of these types of main group organometals causes a more rapid drop in concentration due to precipitation of the dialkylmagnesium from solution. In the case of the mixed di-n-butyl-/di-sec-butyl-magnesium complexes, this precipitate on analysis conforms to an n-butyl-/sec-butyl- ratio in the complex of about 2:1. The complex is soluble in benzene and cyclohexane. Apparently the 2:1 complex is held in a soluble, but metastable, form by the presence of excess di-sec-butylmagnesium.

Admixture of, for example, 10 mole % of n-hexyl chloride or n-octyl chloride or higher n-alkyl chlorides with the n-butyl chloride halide charge to be reacted with magnesium metal delays or prevents this precipitation, both at ambient and refrigeration temperatures, and a like situation obtains where the corresponding bromides or iodides are employed.

It is believed that the di-n-hexylmagnesium or the di-n-octylmagnesium, for example, formed during the reaction between n-hexyl chloride or n-octyl chloride, as the case may be, and magnesium metal acts as a "sta-

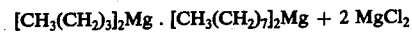

bilizing" agent to prevent the precipitation of the 2:1 di-n-butylmagnesium/di-sec-butylmagnesium complex by preferential complexation with di-n-butylmagnesium.

Magnesium metal utilized in the first step of the method of our present invention can be in particulate from or in the form of powder, either coarse (through 50 mesh or greater), or very fine (through 320 mesh), although it is preferable to use an intermediate grade of through 100 mesh, both from safety and economic aspects.

Branched dialkylmagnesium compounds employed in step 2 of the method of our present invention can be derived from the utilization in said step 2 of alkyllithium compounds such as sec-butyl- and tert-butyllithium with branching at the alpha carbon atom, as well as from the utilization of other branched organolithium compounds such as tert-amyllithium, 2-ethylhexyllithium, neopentyllithium, menthyllithium, and neophyllithium. The particularly advantageous branched organolithiums are sec- and tert-butyllithium.

It is important, in the particularly advantageous embodiments of the practice of the present invention, that the $C_1$-$C_4$ and the $C_6$-$C_{18}$ alkyl halides utilized in the initial step of the reaction as, for instance, butyl chloride and octyl chloride, both be normal or linear, and that the liquid hydrocarbon solvents be acyclic. However, in this latter aspect of our invention, one can use, so far as the composition itself is concerned, aromatic or cyclic hydrocarbons such as, for instance, benzene, toluene, cyclohexane, cycloheptane, and cyclooctane, or compatible mixtures thereof. In the second step, it is likewise the particularly advantageous embodiment of our invention that the liquid hydrocarbon solvent or solvents used also be acyclic so that the final solution, after filtering off the lithium halide which is formed in the second step of the method, serves to produce a final solution in an acyclic liquid hydrocarbon solvent of a complex of (a) a di-n-alkylmagnesium where the alkyl contains from 1 to 4 carbon atoms, (b) a di-n-alkylmagnesium where the alkyl contains from 6 to 18 carbon atoms, and (c) a di-secondary or di-tertiary organomagnesium compound, especially di-sec- or di-tert-butylmagnesium. However, here, again, in the broader aspects of our invention, aromatic or cyclic hydrocarbons, or compatible mixtures thereof, can be used as the solvents. When used in particular polymerizations, however, particular types of the hydrocarbon solvents may be indicated for optimal production of certain polymerizates.

The following Examples, except for Example 1a which is included for comparative purposes of showing the results when our invention is not practiced in relation to the results when our invention is practiced, show illustrative runs carried out in accordance with out invention. It will, of course, be understood that many other stable diorganomagnesium compositions can be made pursuant to our invention utilizing different alkyl halides, different secondary and tertiary organolithiums, different acyclic liquid hydrocarbon solvents, and different reaction temperatures, ect. without departing from the guiding principles and teachings disclosed herein. All temperatures recited are in degrees centigrade.

EXAMPLE I

Preparation of Acyclic Liquid Hydrocarbon-Soluble Dibutylmagnesium a. With no $C_6$ or higher alkyl halide present 20 g of magnesium metal powder (−100 mesh) are stirred in 500 ml of Isopar E* solvent containing 3 ml of a 10 wt. % solution of preformed dibutylmagnesium in Isopar E for a period of 30 minutes under an atmosphere of dry nitrogen. The resulting mixture (1.6 Molar in Mg) is heated to boiling and until a gentle reflux is attained (about 120°–121°) and then the heat is turned off. After the mixture has just ceased refluxing (about 120°), 10 ml of a solution (made by mixing 73 ml (64.7g) of n-butyl chloride with 73 ml of Isopar E) is added to the mixture all at once. Within 3 minutes, spontaneous vigorous refluxing begins once again and the n-butyl chloride solution feed is continued, the remainder of the aforesaid n-butyl chloride solution being added over a period of about 37 minutes in order to maintain reflux throughout. The reaction mixture is then stirred and allowed to cool to room temperature. A volume of 550 ml of 1.21 N sec-butyllithium in hexane is then added to the viscous reaction mixture over an approximately 34 minute period. The resulting fluid mixture is stirred for an additional approximately 45 minutes, and is then allowed to settle for about 15 minutes. The product mixture is then filtered over an about a 1-hour period and the solid residue is washed twice with 150 ml of Isopar E (over a period of about 25 minutes) to give a total of 1225 ml of a 1.029 N (total alkalinity) solution of dibutylmagnesium (1.02 N in magnesium). The yield of product obtained is 92% based on the n-butyl chloride and sec-butyllithium added.

\* An isoparaffinic solvent in the $C_8$-$C_9$ region boiling from about 115° to about 142° (Exxon Corp.).

After 7 days standing at ambient temperature, the concentration of the product solution is analyzed and found to have dropped to 0.94 N (total alkalinity) (8% decrease from original value). A precipitate is noted. The product is then placed in a refrigerator (5°) for an additional 7 days, after which the supernatant solution is again analyzed and found to be only 0.61 N (in total alkalinity), an overall decrease from the original titer of 41%.

The following Table A shows the loss of solubility of dibutylmagnesium at two temperatures using a duplicate set of 3 dibutylmagnesium samples of varying concentration from another, larger preparative run, one set of three samples being stored at room temperature (25°), while the other set is stored at 5°.

TABLE A

| Run PP5 Initial Samples (N) | | Concentration (N) After 8 days Storage | % Drop. (From Initial Value) |
|---|---|---|---|
| | 0.94 | 0.76 | 19 |
| 25° | 0.78 | 0.65 | 17 |
| | 0.62 | 0.53 | 15 |
| | 0.94 | 0.41 | 56 |
| 5° | 0.78 | 0.36 | 54 |
| | 0.62 | 0.29 | 53 |

The product precipitates slowly at room temperature and much more rapidly at colder temperatures.

b. With 10 mole % n-octyl chloride present

The above run of part a of this Example I is repeated except that a blend of 11.65 ml n-octyl chloride (10.4 g, 0.07 moles) and 66.29 ml of n-butyl chloride (58.3 g, 0.63 moles) in 78 ml of Isopar E is substituted for the n-butyl chloride/Isopar E charge of the said part a Example. The reaction initiates well and the remainder of said blend of n-octyl chloride and n-butyl chloride in Isopar E is added over a period of about 31 minutes. After the addition is complete, the mixture is heated for an additional approximately 45 minutes at reflux, and then the heat is turned off. When the viscous mixture has cooled to 50°-60°, a volume of 491 ml of 1.14 N sec-butyllithium in Isopar E is added during an approximately 31 minute period. After stirring for an additional approximately 45 minutes, the fluid reaction mixture is filtered over a 30 minute period and the residual solids are washed twice with 150 ml Isopar E. A volume of 1385 ml of a 0.78 N solution (total alkalinity) of dibutylmagnesium (0.77 N in Mg) is obtained for a yield of 85% based on the n-butyl chloride, the n-octyl chloride and the sec-butyllithium used in the preparation.

The product solution does not crystallize from solution after storage for 1 week at 5°.

Data subsequently obtained on the ambient (25°) storage stability of four larger production runs of dibutylmagnesium produced as described in part (b) of this Example I is shown in the following Table B.

TABLE B

| | Dibutylmagnesium-Storage Stability Data | | |
|---|---|---|---|
| | Storage Time | Analyses, N | |
| Run No. | (Days) | Total Base | Magnesium |
| 8A | 0 | 1.06 | 1.04 |
| | 77 | 1.07 | 1.07 |
| 10A | 0 | 1.13 | 1.14 |
| | 67 | 1.12 | 1.13 |
| 12A | 0 | 1.24 | 1.23 |
| | 56 | 1.23 | 1.22 |
| 13A | 0 | 1.25 | 1.23 |
| | 49 | 1.24 | 1.23 |

Essentially no loss is observed due to product precipitation, even over extended periods of time (up to 2.5 months) as contrasted with dibutylmagnesium produced without the presence of dioctylmagnesium, generated from the n-octyl chloride in the n-butyl chloride feed.

EXAMPLE II

Preparation of a 1:1 Di-n-Butylmagnesium-Di-n-Octylmagnesium Complex and Solubilization Thereof in Acyclic Liquid Hydrocarbons To a slurry of 20 g of magnesium powder in 500 ml of Isopar E kept just below the reflux temperature, there is added 15 ml of a blend prepared by dissolving 36.8 ml (32.4 g, 0.35 mole) of n-butyl chloride and 58.2 ml (52 g, 0.35 mole) of n-octyl chloride in 95 ml of Isopar E. The reaction initiates in 1 to 2 minutes with vigorous refluxing. The remainder of the said n-butyl chloride-n-octyl chloride solution is then added over an approximately 38 minute period. Near the end of said addition, added heat is supplied to maintain reflux. Refluxing is maintained for an additional approximately 38 minutes after which heating and stirring of the viscous mixture are discontinued. A volume of 100 ml of 1.143 N sec-butyllithium in Isopar E is then added to thin out the mixture. Then an additional 391 ml of said 1.143 N sec-butyllithium in the Isopar E is added over a 30 minute period. The mixture is filtered over an approximately 23 minute period to separate the solution from byproduct salts. The salts are washed twice with 100 ml of Isopar E to give a total of 1260 ml of solution, assaying 0.85 N in total alkalinity and 0.81 N in Mg (yield 85% on total alkalinity).

On refrigeration of the solution at 5°, no precipitation of product occurs over a 3 day period.

EXAMPLE III

Preparation of an Acyclic Liquid Hydrocarbon-Soluble Dibutylmagnesium Using 15 Mole % n-Octyl Chloride To a mixture of 10 g of magnesium powder in 250 ml of Isopar E at just below the boiling point there is added 7 ml of a solution of 29.5 ml (0.28 moles) of n-butyl chloride and 8.4 ml (0.05 moles) of n-octyl chloride (15 mole % on total chloride charge) in 40 ml of Isopar E. After reaction is initiated, the balance of said n-butyl chloride-n-octyl chloride solution in Isopar E is added at reflux over an approximately 28 minute period. The reaction mixture is refluxed for an additional hour, then cooled to 40°. A volume of 194 ml of 1.36 N sec-butyllithium in Isopar E is then added at 30°-40°. After reaction and filtration, 720 ml of a 0.74 N solution (total alkalinity) is recovered (81%). The solution is stable to precipitation over at least a two week period.

EXAMPLE IV

Preparation of Acyclic Liquid Hydrocarbon-Soluble Dibutylmagnesium Using 10 mole % n-Hexyl Chloride Example III is repeated except that a chloride charge consisting of 31.4 ml (27.5 g, 0.30 moles) of n-butyl chloride and 4.5 ml (4 g, 0.033 moles) of n-hexyl chloride dissolved in an equal volume of Isopar E is employed in place of the n-butyl chloride-n-octyl chloride solution in Isopar E. After initiation, the chloride charge is fed in over a period of about 49 minutes. After 1 hour additional refluxing, the mixture is cooled and 160 ml of 1.62 N sec-butyllithium in Isopar E is added. The thin product mix is filtered in about 11 minutes and the solids are washed once with 100 ml Isopar E. Total volume of filtrate is 680 ml. The concentration of the solution in dibutylmagnesium is 0.77 N and the yield is 89%. The product is stable to precipitation both at ambient and refrigeration temperatures.

EXAMPLE V

Preparation of Acyclic Liquid Hydrocarbon-Soluble Dibutylmagnesium Using n-Butyl- and n-Octyl Bromides To a mixture of 10 g of magnesium powder (−100 mesh) in 300 ml of distilled hexane containing 5 ml of 0.9 N butylmagnesium as activator is added, over a 1-hour period, 28.1 ml (35.7 g, 0.26 moles) of n-butyl bromide and 17.3 ml (19.3 g, 0.026 moles of n-octyl bromide) (90:10 mole % mixture) dissolved in an equal volume of hexane. After reaction is complete, the mixture is cooled to room temperature and 179 ml of 1.62 N sec-butyllithium in Isopar E is then added (based on 100% of the total bromide charged). The yield of product after filtration and washing to remove byproduct bromides is 80% based on a recovered volume of 750 ml of 0.62 N solution. Bromide ion in solution is 0.07%. Solution storage stability is excellent.

EXAMPLE VI

Preparation of Acyclic Liquid Hydrocarbon-Soluble Diethylmagnesium Using n-Ethyl and n-Octyl Bromides The method of Example V is carried out except that the bromide charge consists of 15.6 g of ethyl bromide and 27.6 g of n-octyl bromide. A product stable to precipitation both at ambient and refrigeration temperatures is obtained.

EXAMPLE VII

Preparation of Acyclic Liquid Hydrocarbon-Soluble Dibutylmagnesium Using n-Butyl and n-Decyl Chlorides The method of Exmaple III is carried out except that the chloride charge consists of 25.9 g of n-butyl chloride and 8.8 g of n-decyl chloride. A product stable to precipitation both at ambient and refrigeration temperatures is obtained.

We claim:

1. A stable complex of (a) a di-n-alkylmagnesium in which the alkyl contains from 1 to 4 carbon atoms with (b) a di-n-alkylmagnesium in which the alkyl contains from 6 to 18 carbon atoms.

2. A stable complex according to claim 1, in which the (a) di-n-alkylmagnesium is present in mole proportions exceeding that of the (b) di-n-alkylmagnesium.

3. A stable complex according to claim 1, in which the (a) di-n-alkylmagnesium is di-n-butylmagnesium.

4. A stable complex according to claim 1, in which the (b) di-n-alkylmagnesium is di-n-octylmagnesium.

5. A stable complex according to claim 1, in which the (a) di-n-alkylmagnesium is di-n-butylmagnesium, (b) the di-n-alkylmagnesium is di-n-octylmagenesium, and the mole % of the di-n-octylmagnesium constitutes about 5-25% of the total of both said di-n-alkylmagnesiums.

6. A stable solution comprising a liquid hydrocarbon solution of a complex of (a) a di-n-alkylmagnesium in which the alkyl contains from 1 to 4 carbon atoms, (b) a di-n-alkylmagnesium in which the alkyl contains from 6 to 18 carbon atoms, and (c) a member selected from the group consisting of di-sec- and di-tert- organomagnesium compounds.

7. A stable solution according to claim 6, in which the (a) di-n-alkylmagnesium is di-n-butylmagnesium, the (b) di-n-alkylmagnesium is di-n-octylmagnesium, and the (c) diorganomagnesium compound is di-sec-butylmagnesium.

8. A stable solution according to claim 7, in which the mole % of the di-n-butylmagnesium is from about 50-95% of the total of the di-n-butylmagnesium and di-n-octylmagnesium, and in which the liquid hydrocarbon is acyclic.

9. A stable complex of (a) a di-n-alkylmagnesium in which the alkyl contains from 1 to 4 carbon atoms, with (b) a di-n-alkylmagnesium in which the alkyl contains from 6 to 18 carbon atoms, the mole % of the (a) di-n-alkylmagnesium being from about 50-95% of that of the total of both said dialkylmagnesiums.

10. A stable complex according to claim 9, in which the (a) di-n-alkylmagnesium is di-n-butylmagnesium and the (b) di-n-alkylmagnesium is di-n-octylmagnesium.

11. A stable complex of (a) a di-n-alkylmagnesium in which the alkyl contains from 1 to 4 carbon atoms, (b) a di-n-alkylmagnesium in which the alkyl contains from 6 to 18 carbon atoms, and (c) a member selected from the group consisting of di-sec- and di-tert-organomagnesium compounds, said composition being soluble in acyclic liquid hydrocarbon solvents.

12. A stable complex according to claim 11, in which the (a) di-n-alkylmagnesium is di-n-butylmagnesium, the (b) di-n-alkylmagnesium is di-n-octylmagnesium, and the (c) diorganomagnesium compound is di-sec-butylmagnesium.

13. A stable complex according to claim 12, in which the mole % of the di-n-butylmagnesium is from about 50-95% of the total of the di-n-butylmagnesium and di-n-octylmagnesium.

* * * * *